United States Patent
Woo et al.

(10) Patent No.: US 7,816,559 B2
(45) Date of Patent: Oct. 19, 2010

(54) METHOD OF PRODUCING UNSATURATED ACID FROM OLEFIN

(75) Inventors: Boo Gon Woo, Daejeon (KR); Jun Seok Ko, Daejeon (KR); Kyoung Su Ha, Daejeon (KR); Seong Pil Kang, Daejeon (KR); Seok Hwan Choi, Daejeon (KR); Young Bae Kim, Yeosu-si (KR)

(73) Assignee: LG Chem, Ltd. (KR)

( * ) Notice: Subject to any disclaimer, the term of this patent is extended or adjusted under 35 U.S.C. 154(b) by 817 days.

(21) Appl. No.: 11/378,438

(22) Filed: Mar. 17, 2006

(65) Prior Publication Data

US 2006/0211884 A1 Sep. 21, 2006

(30) Foreign Application Priority Data

Mar. 18, 2005 (KR) .................... 10-2005-0022723

(51) Int. Cl.
*C07C 51/16* (2006.01)
(52) U.S. Cl. ..................................... 562/545
(58) Field of Classification Search ............. 562/545
See application file for complete search history.

(56) References Cited

U.S. PATENT DOCUMENTS

| 3,147,084 A | 9/1964 | Franzen et al. |
| 3,801,634 A | 4/1974 | Krabetz et al. |
| 3,871,445 A | 3/1975 | Wanka et al. |
| 4,256,783 A | 3/1981 | Takada et al. |
| 4,837,360 A | 6/1989 | Kadowaki et al. |
| 6,399,818 B2 | 6/2002 | Tanimoto et al. |
| 6,657,080 B2 | 12/2003 | Yunoki |
| 2005/0049435 A1 | 3/2005 | Ha et al. |

FOREIGN PATENT DOCUMENTS

| EP | 0383224 | 8/1990 |
| EP | 0911313 | 4/1999 |

(Continued)

OTHER PUBLICATIONS

International Search Report dated Apr. 26, 2006 for Application No. PCT/KR2006/000979 (All references cited in Search Report are listed above).

(Continued)

*Primary Examiner*—Taylor Victor Oh
(74) *Attorney, Agent, or Firm*—Cantor Colburn LLP

(57) ABSTRACT

Disclosed is a shell-and-tube heat exchanger type reactor that can be used for a process of producing unsaturated acids from olefins via fixed-bed catalytic partial oxidation, which comprises at least one reaction tube, each including at least one first-step catalyst layer, in which olefins are oxidized by a first-step catalyst to mainly produce unsaturated aldehydes, and at least two second-step catalyst layers, in which the unsaturated aldehydes are oxidized by a second-step catalyst to produce unsaturated acids, wherein a first catalyst layer of the second-step catalyst layers, disposed right adjacent to the first-step catalyst layer, has an activity corresponding to 5~30% of the activity of the catalyst layer having a highest activity among the second-step catalyst layers. A method of producing unsaturated acids from olefins by using the reactor is also disclosed.

7 Claims, 1 Drawing Sheet

FOREIGN PATENT DOCUMENTS

| | | |
|---|---|---|
| EP | 1055662 A1 | 5/2000 |
| EP | 1156027 A1 | 11/2001 |
| EP | 1350566 A2 | 10/2003 |
| JP | 02-218428 A | 8/1990 |
| JP | 11-130722 A | 5/1999 |
| JP | 2001-328951 A | 11/2001 |
| JP | 2001-354612 A | 12/2001 |
| JP | 2005-021149 A | 1/2005 |
| KR | 100204728 | 3/1999 |
| KR | 100349602 | 8/2002 |
| KR | 1020040005468 | 1/2004 |
| KR | 1020050024206 | 3/2005 |
| WO | 2004007064 | 1/2004 |

OTHER PUBLICATIONS

Taiwanese Search Report; Application No. 095108984; Filing Date Mar. 16, 2006.

EP Search Report for Application No. 06716429.3 - 2103 dated Jun. 4, 2010.

METHOD OF PRODUCING UNSATURATED ACID FROM OLEFIN

This application claims the benefit of the filing date of Korean Patent Application No. 2005-22723, filed on Mar. 18, 2005, in the Korean Intellectual Property Office, the disclosure of which is incorporated herein in its entirety by reference.

TECHNICAL FIELD

The present invention relates to a process of producing unsaturated acids from olefins via fixed bed partial oxidation in a shell-and-tube heat exchanger type reactor. Also, the present invention relates to a fixed bed shell-and-tube heat exchanger-type reactor used for the above process.

BACKGROUND ART

A process of producing unsaturated acids from vapor phase C3~C4 olefins by using a catalyst is a typical process of catalytic vapor phase oxidation.

Particular examples of such catalytic vapor phase oxidation include a process of producing acrolein and/or acrylic acid by the oxidation of propylene or propane, a process of producing methacrolein and/or methacrylic acid by the oxidation of isobutylene, t-butyl alcohol or methyl-t-butyl ether, a process of producing phthalic anhydride by the oxidation of naphthalene or orthoxylene, and a process of producing maleic anhydride by the partial oxidation of benzene, butylene or butadiene.

Generally, catalytic vapor phase oxidation is carried out by charging one or more kinds of granular catalysts into a reactor tube, supplying feed gas into a reactor through a reaction tube, and contacting the feed gas with the catalyst in the reactor tube. Reaction heat generated during the reaction is removed by heat exchange with a heat transfer medium, whose temperature is maintained at a predetermined temperature. The heat transfer medium for such heat exchange is provided on the outer surface of the reaction tube so as to perform heat transfer. The reaction mixture containing a desired product is collected and recovered through a duct, and then sent to a purification step. Since the catalytic vapor phase oxidation is a highly exothermic reaction, it is very important to control the reaction temperature in a certain range and to reduce the size of the temperature peaks at hot spots generated in reaction zones. It is also important to accomplish heat dispersion at a point to be subjected to heat accumulation due to the structure of the reactor or that of the catalyst layer.

The catalysts that may be used to perform partial oxidation of olefins include composite oxides containing molybdenum and bismuth, molybdenum and vanadium, or mixtures thereof.

Generally, (meth)acrylic acid, a final product, is produced from propylene, propane, isobutylene, t-butyl alcohol or methyl-t-butyl ether (referred to as 'propylene or the like', hereinafter) by a two-step process of vapor phase catalytic partial oxidation. More particularly, in the first step, propylene or the like is oxidized by oxygen, inert gas for dilution, steam and a certain amount of a catalyst, so as to produce (meth)acrolein as a main product. Then, in the second step, the (meth)acrolein is oxidized by oxygen, inert gas for dilution, steam and a certain amount of a catalyst, so as to produce (meth)acrylic acid. The catalyst used in the first step is a Mo—Bi-based oxidation catalyst, which oxidizes propylene or the like to produce (meth)acrolein as a main product. Also, some acrolein is continuously oxidized on the same catalyst to partially produce (meth)acrylic acid. The catalyst used in the second step is a Mo—V-based oxidation catalyst, which mainly oxidizes (meth)acrolein in the mixed gas containing the (meth)acrolein produced from the first step to produce (meth)acrylic acid as a main product.

A reactor for performing the aforementioned process is provided either in such a manner that both the two-steps can be performed in one catalytic tube, or in such a manner that the two steps can be performed in different catalytic tubes, respectively. U.S. Pat. No. 4,256,783 discloses such a reactor.

Meanwhile, (meth)acrylic acid producers have made diversified efforts to improve the structure of the above reactor so as to increase the production yield of (meth)acrylic acid obtained from the reactor; to propose the most suitable catalyst to induce oxidation; or to improve operating conditions of the process.

As a part of such prior efforts, the high space velocity or the high concentration of propylene or the like supplied into the reactor is used. In this case, there is a problem in that oxidation occurs rapidly in the reactor, making it difficult to control the resultant reaction temperature. There is another problem in that hot spots are generated in the catalyst layers of the reactor and heat accumulation occurs in the vicinities of the hot spots, so that the production of byproducts, such as carbon monoxide, carbon dioxide and acetic acid increases at high temperature, thereby reducing the yield of (meth)acrylic acid.

Furthermore, when (meth)acrylic acid is produced by using propylene or the like to a high space velocity and high concentration, reaction temperature increases abnormally in the reactor, thereby causing various problems, such as the loss of active ingredients from the catalyst layer, or a reduction in the number of active sites caused by the sintering of metal components, resulting in degradation in the quality of the catalyst layer.

Accordingly, in the production of (meth)acrylic acid, control of the reaction heat in the relevant reactor is the most important to ensure high productivity. Particularly, both the formation of hot spots in the catalyst layers and the heat accumulation in the vicinities of the hot spots should be inhibited, and the reactor should be effectively controlled so that the hot spots do not cause the so-called runaway phenomenon of the reactor (runaway: a state in which the reactor cannot be controlled or the reactor explodes due to a highly exothermic reaction). Therefore, it is very important to inhibit the generation of the hot spots and heat accumulation in the vicinities of the hot spots so as to extend the lifetime of catalysts and to inhibit side reactions, and thus to increase the yield of (meth)acrylic acid. To achieve these objectives, many attempts have been steadily made.

Meanwhile, in order to operate the above processes more effectively, the reaction system should be designed in such a manner that it is suitable for oxidation with excessive heat generation. Particularly, in order to inhibit the deactivation of a catalyst caused by excessive heat generation, it is necessary to establish an efficient heat control system capable of controlling extremely high temperatures at hot spots, heat accumulation in the vicinities of the hot spots, and a runaway phenomenon. To provide an efficient heat control system, many studies have been made to establish a circulation pathway of molten salts by mounting various baffles (e.g., U.S. Pat. No. 3,871,445), to design an oxidation reactor integrated with a cooling heat exchanger (e.g., U.S. Pat. No. 3,147,084), to provide a multi-stage heat control structure using an improved heat exchanger system (e.g., Korean patent application No. 10-2002-40043, and PCT/KR02/02074), and to control the structure of a catalyst layer and the reaction temperature, so as to be suitable for an improved heat exchange system (e.g., Korean patent application No. 10-2004-0069117).

DISCLOSURE OF THE INVENTION

In view of the above-mentioned problems occurring in the prior art, the present inventors have made improvements in a fixed-bed shell-and-tube heat exchanger type reactor of producing unsaturated acids from olefins. An objective of the present invention is to provide a fixed-bed shell-and-tube heat exchanger-type reactor of producing unsaturated acids from olefins, which comprises a catalyst layer with no need for a layer of inactive materials, which has been packed in the reactor prior to a catalyst layer in a second-step reaction zone, by controlling the activity of an inlet portion of the catalyst layer of the second-step reaction zone and/or by controlling the second-step reaction zone in a multi-stage manner.

According to an aspect of the present invention, there is provided a shell-and-tube heat exchanger type reactor that can be used for a process of producing unsaturated acids from olefins via fixed-bed catalytic partial oxidation, which comprises at least one reaction tube, each including at least one first-step catalyst layer, in which olefins are oxidized by a first-step catalyst to mainly produce unsaturated aldehydes, and at least two second-step catalyst layers, in which the unsaturated aldehydes are oxidized by a second-step catalyst to produce unsaturated acids, wherein a first catalyst layer of the second-step catalyst layers, disposed right adjacent to the first-step catalyst layer, has an activity corresponding to 5~30% of the activity of the catalyst layer having a highest activity among the second-step catalyst layers. There is also provided a method of producing unsaturated acids from olefins by using the same reactor.

As used herein, the term "activity" refers to the percent ratio of the conversion of unsaturated aldehydes into unsaturated acids in a relevant catalyst layer, divided by the conversion in the catalyst layer having the highest activity under the same conditions.

Hereinafter, the present invention will be explained in more detail.

The present invention provides a shell-and-tube heat exchanger type reactor that can be used for a process of producing unsaturated acids from olefins via fixed-bed catalytic partial oxidation, the reactor being an integrated reactor, in which a first-step reaction of mainly producing unsaturated aldehydes from olefins and a second-step reaction of producing unsaturated acids from the unsaturated aldehydes are carried out sequentially in one reaction tube. The present invention makes an improvement in the second-step reaction zone.

(1) Catalyst Layer in Second-Step Reaction Zone

The present invention is characterized in that the first catalyst layer of at least two second-step catalyst layers, disposed right adjacent to the first-step catalyst layer, has an activity corresponding to 5~30% of the activity of the catalyst layer having the highest activity among the second-step catalyst layers.

In general, the inlet portion (herein, the second catalyst layer of the second-step catalyst layers) of the second-step reaction zone has a high concentration of unsaturated aldehydes and oxygen, thereby causing a severe reaction. Thus, the inlet portion contributes to the total conversion of the unsaturated aldehydes to a degree of 40% or higher. Therefore, it is preferable to control the reaction in the inlet portion of the second-step reaction zone in such a manner that the peak temperature of the catalyst is significantly lower than the calcination temperature of the catalyst.

The temperature of unsaturated aldehyde-containing gas produced from the first-step reaction generally ranges from 300° C. to 380° C., which is the same as the temperature of the first-step catalyst layer. The temperature of the second-step catalyst layer suitably ranges from 250° C. to 350° C. Therefore, the unsaturated aldehyde-containing gas produced from the first-step reaction should be cooled so that the temperature of the gas is adjusted to the reaction temperature of the second-step reaction zone. For this, an inactive layer formed of inactive materials has been introduced between the first-step reaction zone and the second-step reaction zone according to the prior art. However, according to the present invention, a catalyst layer, which has the activity of the second-step catalyst but a significantly lower catalytic activity, for example by mixing inactive materials with the second-step catalyst, is introduced into a reactor. By doing so, it is possible to reduce the temperature of the unsaturated aldehyde-containing gas produced from the first-step reaction, while decreasing the load of conversion of the unsaturated aldehydes in the second catalyst layer of the second-step catalyst layers, in which unsaturated acids are produced to a full scale.

In other words, according to the present invention, at least two second-step catalyst layers are disposed right adjacent to the first-step catalyst layer with no use of an inactive layer, wherein the first catalyst layer of the second-step catalyst layers performs pre-reaction of a part of the unsaturated aldehydes into unsaturated acids, so that the second catalyst layer of the second-step catalyst layers can perform the reaction of producing unsaturated acids from unsaturated aldehydes to a full scale under mild conditions with a reduced load of conversion of unsaturated aldehydes. Particularly, the first catalyst layer of the second-step catalyst layers causes the unsaturated aldehyde-containing gas produced from the first-step reaction to have a temperature and a pressure, suitable for the reaction conditions of the second catalyst layer of the second-step catalyst layers. For example, the unsaturated aldehyde-containing gas (reaction product of the first-step reaction) present at about 300° C. can be adapted to the reaction temperature of the second-step reaction zone, which is lower than the above temperature by about 30~50° C., by virtue of the first catalyst layer of the second-step catalyst layers. Therefore, it is possible to prevent excessive heat generation in the second-step reaction zone and to extend the lifetime of the second-step catalyst.

Additionally, when the load of conversion of the unsaturated aldehydes in the second catalyst layer of the second-step catalyst layers decreases, it is possible to sufficiently increase the temperature of a heat transfer medium in the shell space corresponding to the second catalyst layer of the second-step catalyst layers, resulting in an increase in the conversion, and thus an increase in the yield of unsaturated acids.

Herein, it is preferable that the first catalyst layer of the second-step catalyst layers shows a drop of the load of conversion of unsaturated aldehydes (i.e., conversion of unsaturated aldehydes into unsaturated acids, caused by the first layer of the second-step catalyst layers) of 5~30%.

Also, it is preferable that the first catalyst layer of the second-step catalyst layers has a catalytic activity corresponding to 5~30% of the catalytic activity of the catalyst layer having the highest activity among the second-step catalyst layers, so that the aldehyde-containing mixed reaction gas introduced into the second catalyst layer of the second-step catalyst layers can be cooled to a temperature suitable for oxidation.

The unsaturated aldehyde-containing gas, which is a reaction product obtained from the first-step reaction zone (i.e., gas containing unsaturated aldehydes, oxygen, nitrogen, steam, unsaturated acids, acetic acid, carbon dioxide, carbon monoxide and a small amount of byproducts), has a temperature higher than the HTS (heat transfer salt) present at the inlet of the second-step reaction zone by 20° C. or more. Hence, the first catalyst layer of the second-step catalyst layers should be designed so as to inhibit an excessive exothermic reaction. For this reason, it is preferable for the first catalyst layer of the second-step catalyst layers to have a catalytic activity corresponding to 5~30% of the catalytic activity of the catalyst layer having the highest activity among the second-step catalyst layer.

For example, when mixing catalyst particles with inactive material particles to provide the first catalyst layer of the second-step catalyst layers, it is possible to use the catalyst particles to an amount of 5~30 wt %.

Methods of reducing the activity of the first catalyst layer of the second-step catalyst layers include: a method of mixing the same catalytically active component as used in another catalyst layer of the second-step catalyst layers with inactive materials and packing the resultant mixture into the first catalyst layer; a method of forming the first catalyst layer by using a catalyst having a catalytically active component or a composition, different from the active component or the composition used in another catalyst layer of the second-step catalyst layers; a method of forming the first catalyst layer by using a catalytically active material having different particle sizes or volumes, or catalyst pellets having different particle sizes or volumes; or a method of modifying catalyst calcination temperatures. When the first catalyst layer of the second-step catalyst layers is mixed with inactive materials, the catalytically active component may be mixed with inactive material powder before pelletizing the catalyst. Otherwise, the pellets of inactive materials may be mixed with catalyst pellets. In the latter case, the catalyst pellets include not only catalysts comprising catalytically active components alone but also supported catalysts comprising catalytically active components supported on some carriers. The shapes of such catalyst pellets include a spherical shape, hollow cylindrical shape, cylindrical shape or other particle shapes.

The inactive materials that may be used in the first catalyst layer of the second-step catalyst layers include alumina, silica alumina, stainless steel, iron, steatite, porcelain and various ceramic products. The pellets of such inactive materials may take the form of spheres, cylinders, rings, rods, plates, iron nets and agglomerates with a suitable size. If desired, inactive materials having different forms may be used in combination at an adequate mixing ratio.

Meanwhile, the first catalyst layer of the second-step catalyst layers preferably has a length corresponding to 5~50% of the length of the reaction tube of the second-step reaction zone.

The first catalyst layer of the second-step catalyst layers is the layer having a reduced catalytic activity so as to prevent degradation in the thermal stability caused by an excessive reaction heat, which is generated by chemical reactions in the catalyst layer. However, it is preferable for the first catalyst layer to provide a conversion ratio of reactants to a degree of 5% or more, in order to ensure the effect of stabilizing the temperature in the second catalyst layer of the second-step catalyst layers. The length of the first catalyst layer depends on the activity of the corresponding catalyst. In order to provide a conversion ratio of about 5% by the first catalyst layer, based on the total conversion ratio of the second-step reaction, the first catalyst layer should have a length corresponding to at least 5% of the length of the reaction tube of the second-step reaction zone, with the proviso that the first catalyst layer has an activity as disclosed herein. However, when the length of the first catalyst layer is too long relative to the total length of the second-step catalyst layer, the overall activity of the total catalyst layer decreases, which may result in a significant decrease in conversion ratio. Therefore, it is preferable that the first catalyst layer of the second-step catalyst layers is less than 50% of the length of the second-step reaction zone. In other words, high-activity catalyst layers of the second-step catalyst layers, except the first catalyst layer, should be provided to a proportion of at least 50%, so as to obtain a conversion ratio of at least 95%.

As described above, the catalyst layer according to the present invention avoids a need for an inactive layer for cooling between the first-step reaction zone and the second-step reaction zone, and makes it possible to reduce the length of the catalytic reaction tube. Therefore, the reactor according to the present invention is very cost-efficient.

(2) Partition for Dividing First-Step Reaction Zone from Second-Step Reaction Zone, and Placement of First Catalyst Layer of Second-Step Catalyst Layers The composition, temperature and pressure of feed mixture to the second-step reaction zone, namely, those of a resultant product in the first-step reaction zone in which unsaturated aldehydes are mainly produced from olefins, depend on those of feed mixture to the first-step reaction zone. Hence, it is preferable to change the temperature condition of a heat transfer medium in the second-step reaction zone in order to establish new optimal process conditions flexibly depending on variations in the external environment and feed mixture conditions.

According to another aspect of the present invention, the shell space of the reactor is divided axially by using a partition into two shell spaces, wherein one of the shell spaces mainly comprises the first-step reaction zone and the other of the shell spaces comprises the second-step reaction zone. Herein, the first catalyst layer of the second-step catalyst layers, corresponding to the inlet portion of the second-step reaction zone, is packed into the reaction tube in such a manner that it includes the whole sections of the partition, by which the shell space of the first-step reaction zone is divided from that of the second-step reaction zone. Considering the cost needed for the construction of the reactor, it is preferable for the first catalyst layer of the second-step catalyst layers to occupy the first-step reaction zone by at most 500 mm. Retention time corresponding to about 500 mm may reduce the load of conversion of unsaturated aldehydes to about 10%. When the first catalyst layer of the second-step catalyst layers, which has a low catalytic activity according to the present invention, is disposed in the reaction tube at a position corresponding to the portion having the partition, by which the shell space of the first-step reaction zone is divided from that of the second-step reaction zone, it is possible to prevent a local temperature increase caused by an incomplete heat transfer at the portion having the partition.

(3) Multi-Stage Heat Control for Second-Step Reaction Zone

According to the present invention, the catalyst layer is formed with no use of a cooling layer that has been packed into the reactor prior to the catalyst layer of the second-step reaction zone. For this reason, it is preferable to perform the heat control of the second-step reaction zone in a multi-stage manner, besides controlling the catalytic activity of the first catalyst layer of the second-step reaction zone.

To perform such multi-stage heat control, it is preferable to further divide the shell corresponding to the second-step reaction zone into at least two shell spaces by using partitions, and to set the temperature of the heat transfer medium supplied to each shell space in an independent manner.

By doing so, it is possible to set an optimal temperature depending on the activity of the catalyst packed into the reaction tube of the relevant shell, and thus to increase the yield. Also, it is possible to inhibit heat accumulation at a hot spot and to prevent a so-called runaway phenomenon by virtue of the aforementioned multi-stage heat control.

It is preferable to set the temperature of the heat transfer medium in such a manner that the temperature of the reaction mixture at the beginning of the first catalyst layer of the second-step catalyst layers is higher than the temperature of the heat transfer medium circulating in the first shell space of the second-step reaction zone by 20~70° C. This makes it possible to inhibit an excessive exothermic reaction and to provide a sufficient catalytic activity. On the other hand, it is preferable to set the temperature of the heat transfer media of the subsequent shell spaces high enough to increase the conversion of the unsaturated aldehyde as high as possible.

BEST MODE FOR CARRYING OUT THE INVENTION

Figure 1:
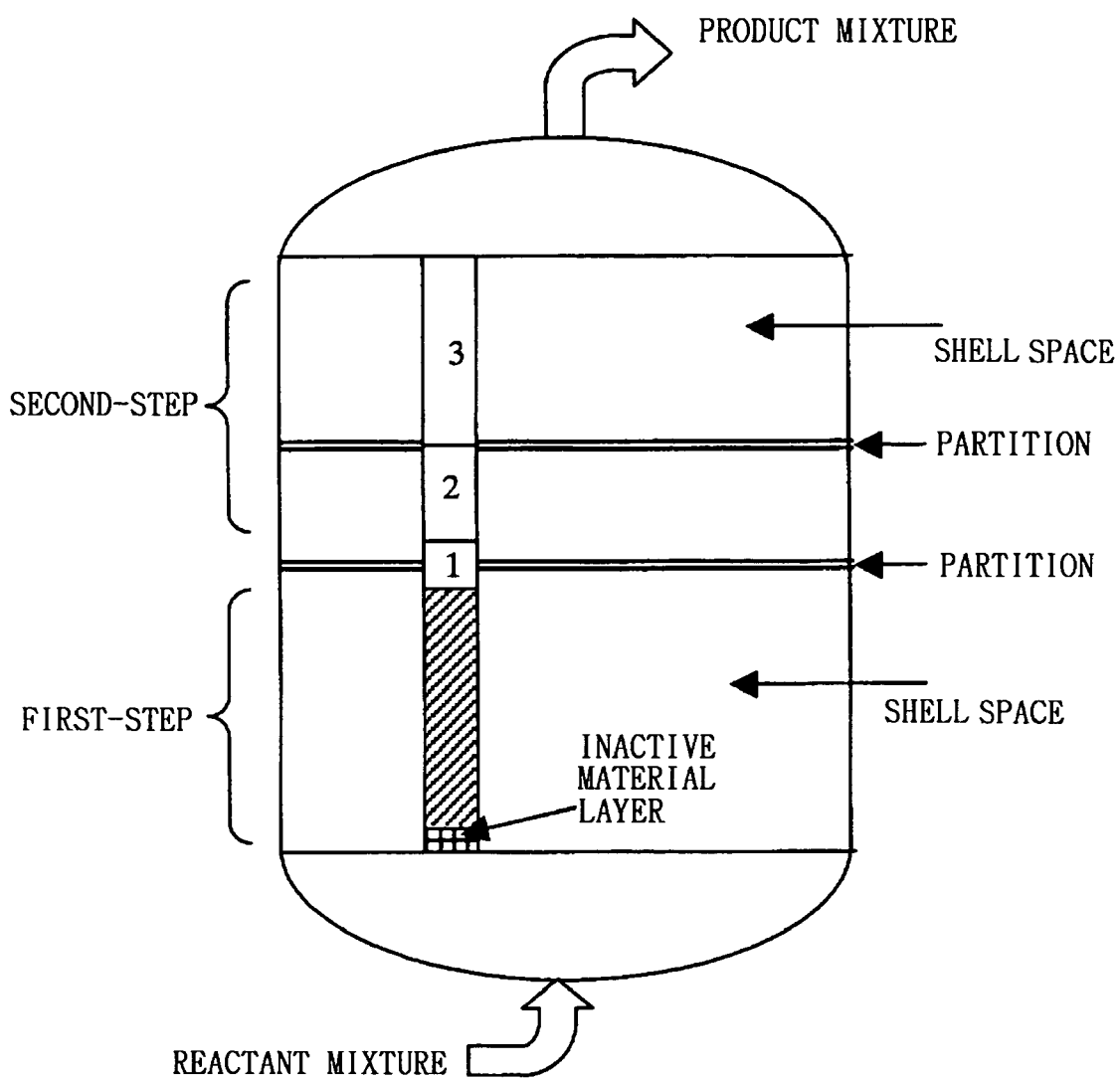
FIG. 1 is a schematic diagram showing the structure of a pilot reactor having one reaction tube, and the structure of a catalyst layer inside the reaction tube, wherein both the first-step reaction and the second-step reaction are carried out in one reactor according to Example 1 of the present invention.

Reference will now be made in detail to the preferred embodiments of the present invention. It is to be understood that the following examples are illustrative only and the present invention is not limited thereto.

Example 1

Use of Mixed Catalyst Layer and Multi-Stage Heat Control

The following experiment was carried out in a pilot reactor having one reaction tube, in which both the first-step reaction and the second-step reaction are performed. The reaction tube had an inner diameter of 26 mm. The first-step catalyst layer and the second-step catalyst layer were packed into the reaction tube to a height of about 3570 mm and about 3125 mm, respectively. The catalyst packed into the first-step reaction zone was a first-step oxidation catalyst based on molybdenum (Mo) and bismuth (bi). Preparation of the catalyst is disclosed in Korean Patent No. 0349602 (Korean Patent Application No. 10-1997-0045132). Each of the three catalyst layers packed into the second-step reaction zone was comprised of a second-step oxidation catalyst based on molybdenum (Mo) and vanadium (V). Preparation of the catalyst is disclosed in Korean Patent No. 0204728 or 0204729.

The second-step catalyst layers were formed by using three catalyst layers that have different activities, increasing when viewed from the inlet to the outlet (see U.S. Pat. Nos. 3,801, 634 and 4,837,360: Control of Catalytic Activity). The first catalyst layer of the second-step catalyst layers, which was the inlet portion of the second-step reaction zone, was comprised of a mixture of 20 wt % of the same catalytic substance as used in the third catalyst layer of the second-step catalyst layers and 80 wt % of an inactive material. Therefore, the first catalyst layer had an activity corresponding to about 20% of the activity of the third catalyst layer. The second catalyst layer of the second-step catalyst layers had an activity corresponding to about 87% based on the activity of the third catalyst layer.

The three catalyst layers of the second-step reaction zone had a height of 500 mm, 700 mm and 1925 mm, respectively, along the axial direction. The mixed layer as the first catalyst layer of the second-step catalyst layers was packed into the reaction tube corresponding to the shell space of the second-step reaction zone to a height of 250 mm, and the remaining height (250 mm) of the first catalyst layer was packed in such a manner that the remaining part covered the partition (partition for dividing the first-step reaction zone from the second-step reaction zone) and some part of the shell space of the first-step reaction zone.

The second-step reaction zone was divided into two independent shell spaces by a partition disposed at the border between the second catalyst layer and the third catalyst layer. Each of the molten salts filled into each of the shell spaces was individually set at a temperature of 275° C. and 270° C.

Starting materials injected into the second-step reaction zone (at the position of the partition for dividing the first-step reaction zone from the second-step reaction zone) included acrolein, acrylic acid, oxygen, steam and nitrogen gas. More particularly, the starting materials included 5.5% of acrolein, 0.9% of acrylic acid, 5.0% of oxygen, 1.0% of byproducts including $CO_x$ and acetic acid, and the remaining amount of nitrogen gas. The space velocity in the second-step reaction zone was 1500 $hr^{-1}$ (standard temperature and pressure, STP). Herein, the space velocity of acrolein as a hydrocarbon reactant supplied to the second-step reaction zone had a space velocity of 81 $hr^{-1}$ (STP) and the mixed feed gas had a pressure of 0.4 $kgf/cm^2G$.

In the second-step reaction zone, two catalyst layers except the first catalyst layer (mixed layer) showed temperature peaks at a temperature of 309.4° C. and 321.7° C. along the axial direction. When propylene was introduced into the first-step reaction zone to an amount of 7.0%, yield of acrylic acid was 86.2%. Yields of byproducts, i.e., $CO_x$ (carbon monoxide and carbon dioxide) and acetic acid were 8.51% and 1.80%, respectively.

The reaction mixture that reached the first catalyst layer of the second-step catalyst layers along the axial direction showed a temperature of 316° C., which was different from the temperature of the first heat transfer medium of the second-step reaction zone by 41° C.

Comparative Example 1

Experiment with No Use of Mixed Layer and Multi-Stage Heat Control

The shell space of the second-step reaction zone was a single non-divided shell space. Additionally, a cooling layer formed of inactive particles was disposed between the first-step reaction zone and the second-step reaction zone. The cooling layer was packed into the reactor to a height of 500 mm. More particularly, the cooling layer was packed into the second-step reaction zone to a height of 250 mm, and the remaining part of the cooling layer was packed into the reaction tube ranging from the partition to the first-step reaction zone. The second-step catalyst layers included two different kinds of catalysts, which were the same as used in the second catalyst layer and the third catalyst layer of Example 1, respectively. Both catalyst layers were packed to a height of 700 mm and 2000 mm along the axial direction. The heat transfer medium was set at a temperature of 270° C. under an isothermal condition. Except the foregoing, the experiment was carried out in the same manner as described in Example 1. Additionally, the two kinds of catalysts, which were used in Example 1, were used in this Example to the same total amount.

In the second-step reaction zone, two catalyst layers showed temperature peaks at a temperature of 318.2° C. and 305.2° C. along the axial direction. Yield of acrylic acid was 84.4%. Yields of byproducts, i.e., $CO_x$ (carbon monoxide and carbon dioxide) and acetic acid were 10.4% and 2.03%, respectively.

Comparative Example 2

Experiment with No Use of Mixed Layer and Multi-Stage Heat Control

Comparative Example 1 was repeated, except that the heat transfer medium was set at a temperature of 275° C.

In the second-step reaction zone, two catalyst layers showed temperature peaks at a temperature of 325.1° C. and 324.9° C. along the axial direction. Yield of acrylic acid was 82.9%. Yields of byproducts, i.e., $CO_x$ (carbon monoxide and carbon dioxide) and acetic acid were 11.4% and 2.42%, respectively.

<Discussion>

It can be seen from the above results of Example 1 and Comparative Examples 1 and 2 that Example 1 provides a higher yield of acrylic acid, compared to the other Examples by about 2% or more, and shows the first peak at a significantly stable temperature. Yield of acrylic acid relates directly to the productivity, and thus is very important. Additionally, the first peak temperature is important because it relates to the lifetime of the catalyst. Reactions carried out in the second catalyst layer of the second-step reaction zone according to Example 1 and the first catalyst layer of the second-step reaction zone according to Comparative Examples 1 and 2 contribute the total acrolein conversion by 50% or more. Although the above catalyst layers are relatively short, they provide a relatively high conversion. In these layers, the compositions of acrolein and oxygen are high, resulting in a severe reaction. Thus, in these layers, it is preferable to control the reactions in such a manner that the peak temperature of the catalyst is significantly lower than the calcination temperature of the catalyst. According to Example 1, the peak temperature is 309.4° C. This indicates that the reaction is carried out at a temperature significantly lower than the reaction temperatures in Comparative Examples 1 and 2 (318.2° C. and 325.1° C.). Therefore, because the reaction is carried out at the inlet portion of the catalyst layers, having a high conversion load, under a milder condition, it is possible to extend the lifetime of the catalyst.

Additionally, Example 1 uses a mixed layer comprising a diluted catalyst in the inlet portion, and thus permits a pre-reaction in a catalyst layer having a significantly lower catalytic activity. Hence, it is possible to reduce the load of conversion of acrolein into acrylic acid in the second catalyst layer to a certain degree. Because a part of acrolein is preliminarily converted into acrylic acid under a mild condition provided by the diluted mixed catalyst layer, the second catalyst layer can have a significantly lower load of conversion of acrolein, compared to the loads of Comparative Examples 1 and 2 with no use of a mixed layer. Also, it is possible to obtain a higher conversion by increasing the temperature of the heat transfer medium in the first shell space along the axial direction, resulting in an increase in the yield of acrylic acid. In Example 1, the first heat transfer medium has a temperature of 275° C., which is higher than the corresponding temperature of Comparative Example 1 by 5° C. However, the peak temperature of the catalyst layer according to Example 1 is lower than the corresponding temperature of Comparative Example 1 by about 9° C. This is because the mixed layer allows the reaction to be performed partially.

In Comparative Example 2, the temperature of the heat transfer medium in the shell space of the second-step reaction zone is same as the corresponding temperature of the first shell space of the second-step reaction zone in Example 1 (275° C.). However, due to the lack of the mixed layer in the inlet portion, acrolein reacts severely with oxygen under a high concentration, so that the peak temperature increases to 325.1° C. Such reaction performed at a high temperature may result in a drop in the lifetime of the first catalyst layer having a high load of conversion.

INDUSTRIAL APPLICABILITY

As described above, according to the present invention, there is provided a structure of catalyst layers, a heat control system and a processing condition, adequate to an improved reactor for producing unsaturated acids via two-step oxidation of olefins. Thus, it is possible to obtain a final product in a stable manner even under a high load reaction conditions. Additionally, use of the heat control system prevents the generation of a hot spot or inhibits heat accumulation at the hot spot. Therefore, it is possible to obtain a high productivity of unsaturated acids and to extend the lifetime of a catalyst.

The invention claimed is:

1. A method of producing unsaturated acids from olefins via fixed-bed catalytic partial oxidation in a shell-and-tube heat exchanger type reactor,
   wherein the reactor comprises at least one reaction tube;
   at least one first-step catalyst layer and at least two second-step catalyst layers are packed sequentially into each reaction tube without a layer made of inactive materials between the first-step catalyst layer and the second-step catalyst layer;
   in the first-step catalyst layer, olefins are oxidized by a first-step catalyst to mainly produce unsaturated aldehydes, and in the second-step catalyst layer, the unsaturated aldehydes are oxidized by a second-step catalyst to produce unsaturated acids; and
   when the second-step catalyst layers have at least two catalyst layers and the catalyst layer among the second-step catalyst layers, which is disposed right adjacent to the first-step catalyst layer, is named as the first catalyst layer of the second-step catalyst layers, the first catalyst layer of the second-step catalyst layers has an activity corresponding to 5~30% of an activity of a catalyst layer having a highest activity among the second-step catalyst layers,
   wherein the first-step catalyst is a composite oxide based on molybdenum and bismuth, and the second-step catalyst is a composite oxide based on molybdenum and vanadium.

2. The method as claimed in claim 1, wherein the first catalyst layer of the second-step catalyst layers provides a drop in a load of conversion of unsaturated aldehydes, ranging from 5% to 30%.

3. The method as claimed in claim 1, wherein a shell space of the reactor is divided axially by a partition into two shell spaces one of the shell spaces mainly comprises the first-step reaction zone and the other of the shell spaces comprises the second-step reaction zone;

and the first catalyst layer of the second-step catalyst layers is packed into the reaction tube in such a manner that it includes the whole sections of the partition, by which the shell space of the first-step reaction zone is divided from that of the second-step reaction zone.

4. The method as claimed in claim 3, wherein the first catalyst layer of the second-step catalyst layers is paced into the reactor in such a manner that the catalyst layer occupies the first-step reaction zone by at most 500 mm.

5. The method as claimed in claim 1, wherein the shell space of the second-step reaction zone is divided into at least two shell spaces by using at least one partition, and each heat transfer medium filled in each shell space is set at a different temperature in independent manner.

6. The method as claimed in claim 5, wherein the temperature of the reaction mixture at the beginning of the first catalyst layer of the second-step catalyst layers is higher than the temperature of the heat transfer medium circulating in the first shell space of the second-step reaction zone by 20~70° C.

7. The method as claimed in claim 1, wherein the first catalyst layer of the second-step catalyst layers has a length corresponding to 5~50% of the length of the reaction tube of the second-step reaction zone.

* * * * *